United States Patent [19]
Allard et al.

[11] Patent Number: 5,476,462
[45] Date of Patent: * Dec. 19, 1995

[54] SPINAL IMPLANT SYSTEM

[75] Inventors: Randall N. Allard, Plymouth; Anthony L. Koser, Warsaw; Joseph R. Korotko, Fort Wayne; Antony J. Lozier, Warsaw, all of Ind.

[73] Assignee: Zimmer, Inc., Warwaw, Ind.

[ * ] Notice: The portion of the term of this patent subsequent to Jan. 25, 2011, has been disclaimed.

[21] Appl. No.: 108,134

[22] Filed: Aug. 16, 1993

Related U.S. Application Data

[63] Continuation of Ser. No. 906,901, Jun. 30, 1992, Pat. No. 5,281,222.

[51] Int. Cl.⁶ .............................. A61B 17/56; A61F 2/28
[52] U.S. Cl. ............................ 606/60; 606/61; 623/16
[58] Field of Search .................... 606/54–59, 61, 606/72, 73; 623/16

[56] References Cited

U.S. PATENT DOCUMENTS

| | | | |
|---|---|---|---|
| 731,635 | 6/1903 | Vandergrift . | |
| 4,269,178 | 5/1981 | Keene | 128/69 |
| 4,361,141 | 11/1982 | Tanner | 606/61 |
| 4,404,967 | 9/1983 | Bacal et al. | 128/69 |
| 4,411,259 | 10/1983 | Drummond | 606/61 |
| 4,641,636 | 2/1987 | Cotrel | 606/61 |
| 4,815,453 | 3/1989 | Cotrel | 606/61 |
| 5,010,879 | 4/1991 | Moriya | 606/61 |
| 5,047,029 | 9/1991 | Aebi et al. | 606/61 |
| 5,074,864 | 12/1991 | Cozad | 606/61 |
| 5,112,332 | 5/1992 | Cozad | 606/61 |
| 5,116,334 | 5/1992 | Cozad | 606/61 |
| 5,122,131 | 6/1992 | Tsou | 606/61 |
| 5,147,359 | 9/1992 | Cozad | 606/61 |
| 5,154,718 | 10/1992 | Cozad | 606/61 |
| 5,257,993 | 11/1993 | Asher | 606/61 |
| 5,281,222 | 1/1994 | Allard | 606/61 |

FOREIGN PATENT DOCUMENTS

| | | | |
|---|---|---|---|
| 0348581A2 | 1/1990 | European Pat. Off. | A61F 5/02 |
| 537593 | 5/1922 | France . | |

*Primary Examiner*—Michael A. Brown
*Attorney, Agent, or Firm*—Margaret L. Geringer

[57] ABSTRACT

A spinal implant system including components designed to be affixed to the spinal column. The system includes spinal rods, attachment devices, and interpositional sleeves for securing the attachment devices to the rods. The attachment devices may be various types of spinal hooks, screws, couplers, rod connectors, clamps, or other such devices.

7 Claims, 3 Drawing Sheets

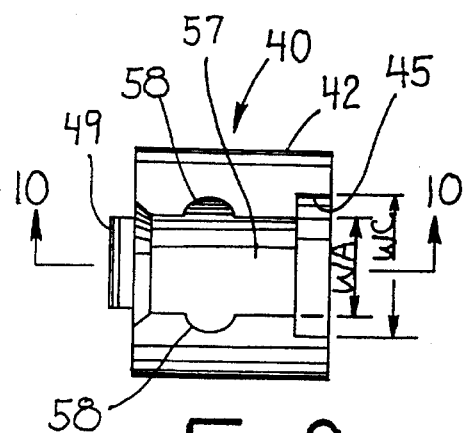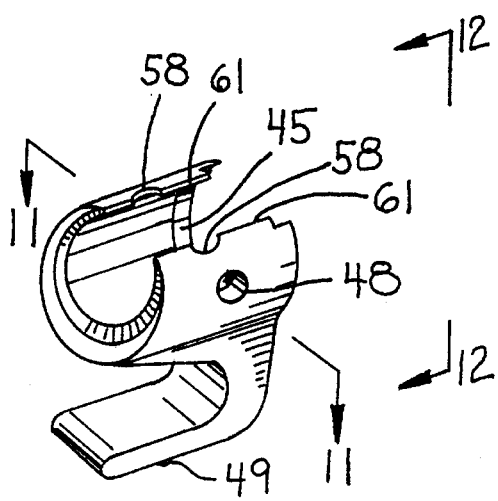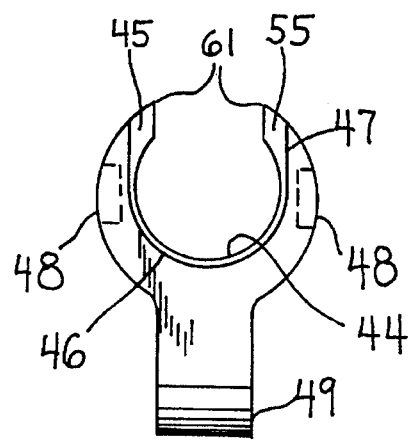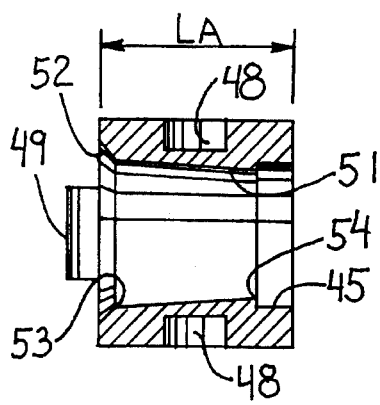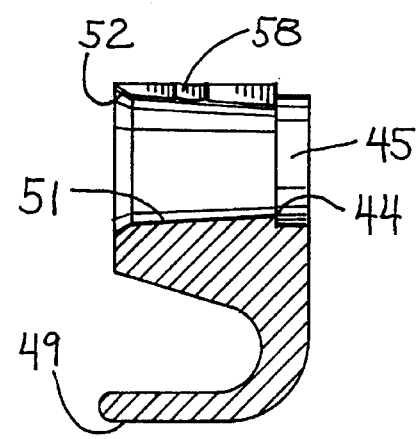

5,476,462

SPINAL IMPLANT SYSTEM

This is a continuation of application Ser. No. 07/906,901 filed Jun. 30, 1992 U.S. Pat. No. 5,281,222.

BACKGROUND OF THE INVENTION

The present invention relates to a spinal implant system, and is suitable for use in treatments for correcting various spinal deformities. In particular, this invention relates to a spinal system of the type that includes an interpositional sleeve for securing various types of attachment devices to a spinal rod.

The use of an interpositional sleeve to secure a spinal attachment device to a rod is taught in the prior art, such as in U.S. Pat. Nos. 5,112,332 and 5,116,334 to Cozad et al. The present invention is a modification and improvement of these Cozad et al. patents, and as such these two U.S. Pat. Nos. 5,112,332 and 5,116,334, are incorporated herein by reference. Both of these Cozad et al. patents, as well as the present invention, are assigned to Zimmer, Inc. These two Cozad et al. patents are both divisional of U.S. Pat. No. 5,074,864 to Cozad et al.

These Cozad et al. patents disclose a spinal implant system which includes a tapered split sleeve having a separate, discrete lock member or lock nut securable over the sleeve. The lock member interacts with the open back attachment device by acting on an exterior surface of the attachment device to secure an interference frictional interconnection between the tapered sleeve and the attachment device to secure the device to the rod.

The following other spinal systems are known which disclose the use of an interpositional sleeve:

U.S. Pat. No. 5,010,879 to Moriya et al. discloses a spinal system having a wedge-like slit sleeve having a cylindrical body with a flange 7a on one end and a tapered portion 8a on the other end. The wedge-like member is forcibly inserted at the tapered end thereof between a spinal hook and a rod.

U.S. Pat. Nos. 4,815,453 and 4,641,636 to Cotrel disclose a spinal system which includes a sleeve 30 having a conical part 31. A pressure screw 25 is provided to selectively fix the anchoring members in position on the spinal rod or pin, which has a roughened surface.

U.S. Pat. No. 4,404,967 to Bacal et al. discloses a spinal system having a split or cut sleeve 3 with skew recesses 4 made along the cut. The inner surfaces of recesses 4 constitute bearing surfaces for a pin 2 which protrudes from the spinal rod 1. A conical end of the sleeve fits into a corresponding recess in the hook.

U.S. Pat. No. 4,269,178 to Keene discloses an open back spinal hook having a sleeve which is slidable along the spinal rod and into the hook. A lock nut may then be used to secure the position of the sleeve.

OBJECTS OF THE INVENTION

A principal object of this invention is to provide a spinal implant system with a secure attachment mechanism that is easy to use, but effective.

Another object of the invention is to provide an interpositional sleeve that can be inserted between a spinal attachment device and a spinal rod to secure the attachment device to the rod without the need for any additional separate locking member, and thus with the securing features built integrally into the features of the sleeve and attachment device themselves.

A further object of the invention is to provide such an interpositional spinal sleeve with a first taper and a second reverse taper, such that the narrow ends of each taper converge to enable the sleeve to be removed from the attachment device, if necessary.

A still further object of the invention is to provide an attachment device which provides a first position for partially seating the sleeve, plus a second position for fully seating the sleeve member between the rod and the attachment device.

An additional object of the invention is to provide a sleeve for positioning between a rod and an attachment device, wherein the sleeve can snap fit laterally onto the rod, rather than have to slide the sleeve onto the rod from one of the ends of the rod to the desired position.

SUMMARY OF THE INVENTION

The present invention provides a spinal implant system including components designed to be affixed to the spinal column. The system includes spinal rods, attachment devices, and interpositional sleeves for securing the attachment devices to the rods. The attachment devices may be various types of spinal hooks, screws, couplers, rod connectors, clamps or other such devices. The attachment device provides two discrete positions for positioning the sleeve, a first partially seated position and a second fully seated position. The sleeve can advantageously be snap fit onto the rod in the desired location. In addition, the sleeve has a first taper and a second reverse taper with the narrow ends of each taper converging to form a reduced portion. The reduced portion may further include a recessed transition zone. The spinal implant system of the present invention provides a stable and secure way to fix the position of a spinal attachment device onto a spinal rod.

BRIEF DESCRIPTION OF THE DRAWINGS

These features and objects of the invention, as well as others, will become apparent to those skilled in the art by referring to the accompanying drawings:

FIG. 8 is a perspective view of the attachment device of FIG. 1;

FIG. 9 is a top view of the attachment device of FIG. 8;

FIG. 10 is a cross-sectional view taken along lines 10—10 of FIG. 9;

FIG. 11 is a cross-sectional view taken along lines 11—11 of FIG. 8; and

FIG. 12 is an end view of the attachment device of FIG. 8 as viewed from lines 12—12 of FIG. 8.

DETAILED DESCRIPTION OF THE INVENTION

FIGS. 1–12 illustrate a particularly advantageous embodiment of a spinal implant system according to the present invention. The spinal implant system includes a spinal rod 1, an attachment device 40, and an interpositional sleeve 10 for securing the device 40 to rod 1. The attachment device 40 may be one of various types of spinal hooks, screws, couplers, rod connectors, clamps, or other such devices. The present invention is illustrated with the attachment device as a spinal hook with extending hook portion 49; however, it is understood that any suitable attachment device may be utilized in accordance with the present invention.

It is understood in keeping with spinal surgery techniques that a plurality of spinal rods can be used, each with a plurality of spinal attachment devices affixed thereto. The attachment devices may either be used to affix the rods to the spinal column or to affix the position of two rods with respect to each other.

Figure 2:
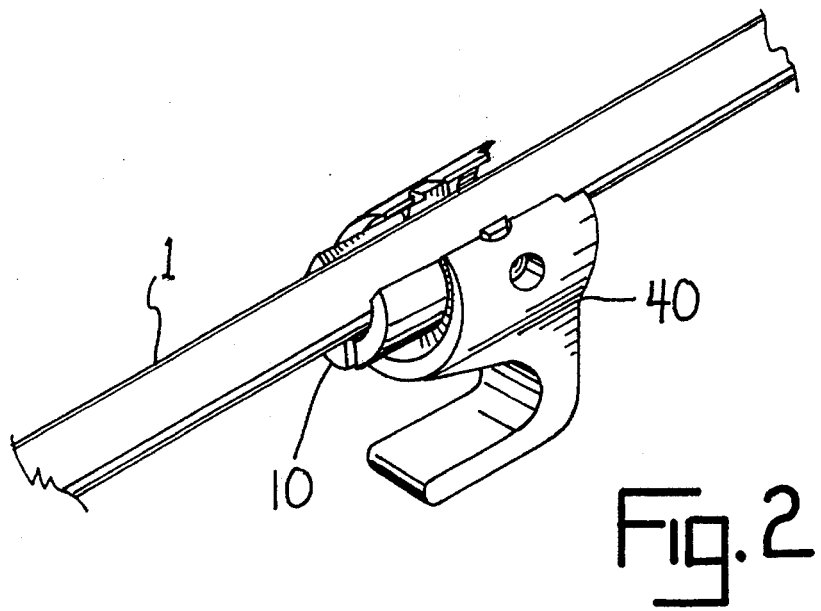
FIG. 2 is a perspective view of the components of FIG. 1 with the sleeve shown in the first partially seated position in the attachment device.
Figure 3:
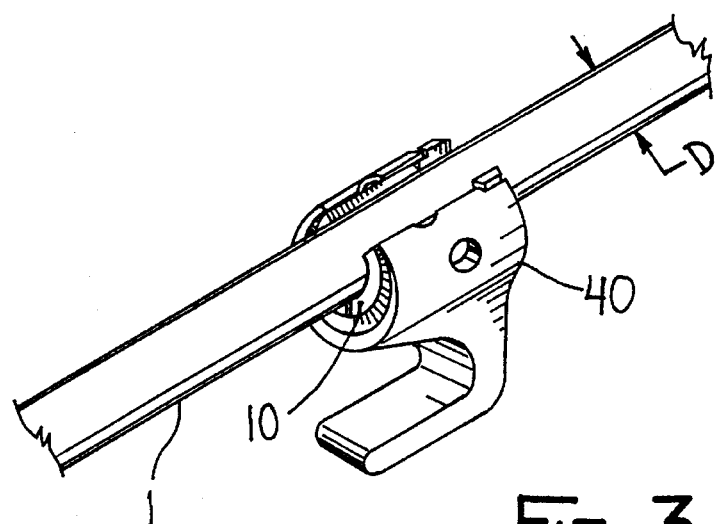
FIG. 3 is a perspective view of the components of FIG. 1 with the sleeve shown in the second fully seated position in the attachment device.
Figure 4:
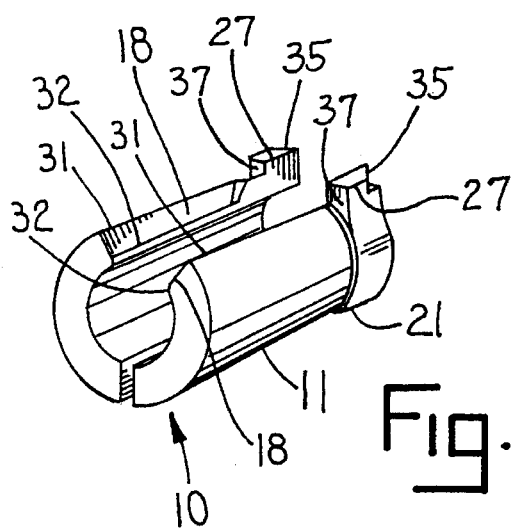
FIG. 4 is a perspective view of the sleeve of FIG. 1.
Figure 5:
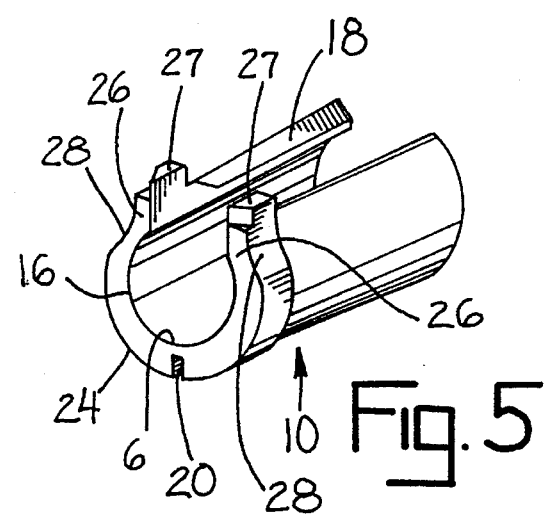
FIG. 5 is a perspective view of the sleeve of FIG. 4 shown from the opposite end.
Figure 6:
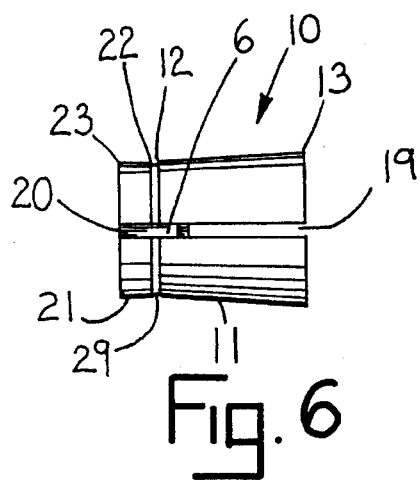
FIG. 6 is a bottom view of the sleeve of FIG. 4.
Figure 7:
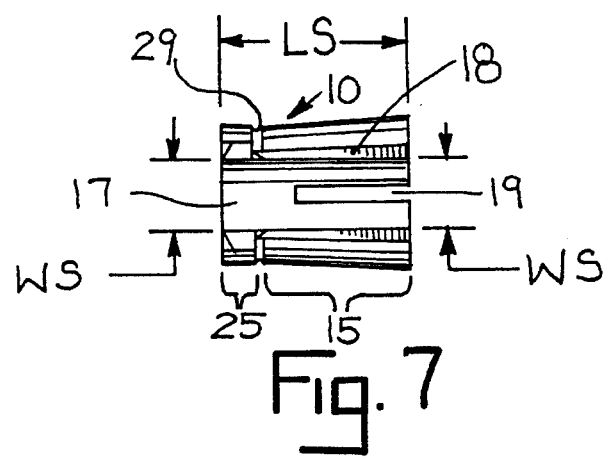
FIG. 7 is a top view of the sleeve of FIG. 4.

The attachment device 40 includes a first position for partially seating the sleeve 10 between the rod i and the attachment device 40, as shown in FIG. 2, and a second position for fully seating the sleeve 10, as shown in FIG. 3.

Figure 1:
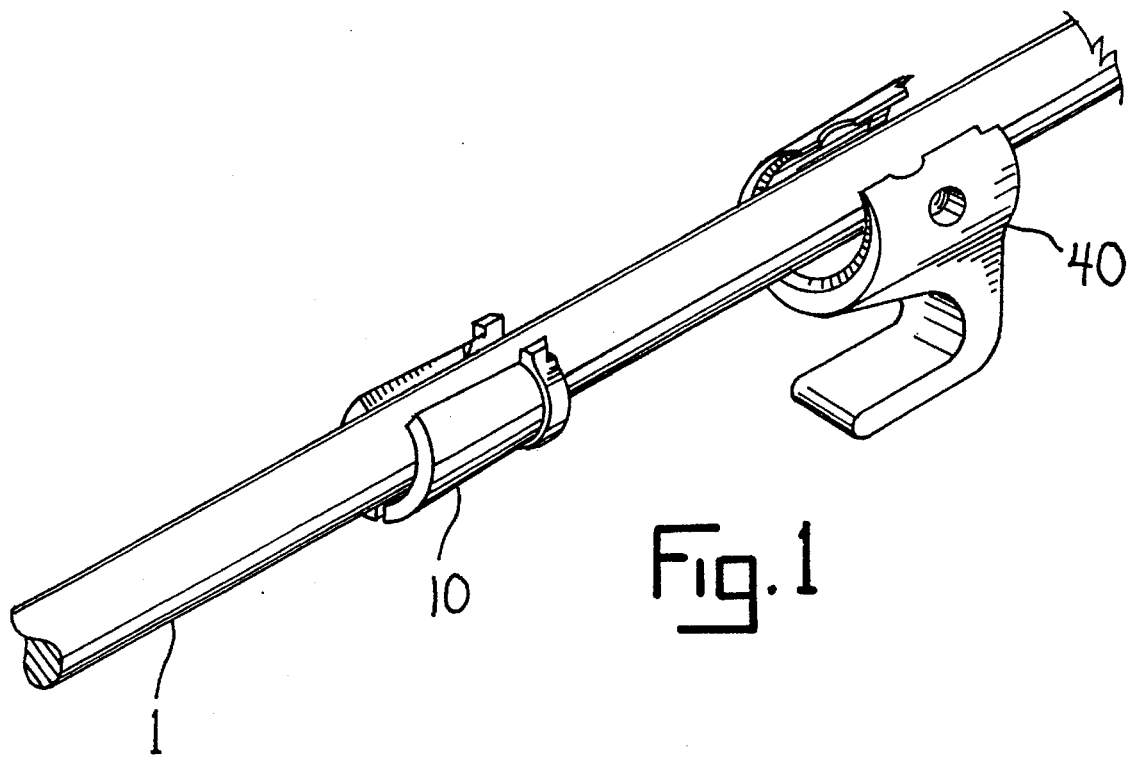
FIG. 1 is a perspective view of a rod, an attachment device, and an interpositional sleeve according to the present spinal implant system invention, and shown prior to insertion of the sleeve in the attachment device.

FIG. 1 shows the sleeve 10 prior to insertion in device 40. The sleeve 10 is positioned on the rod 1, while the attachment device 40 is held in position by a suitable hook holder instrument (not shown). Such hook holder instruments are known in the art and grip the attachment device 40 via recessed gripping holes 48. Then a suitable pusher or cruncher type instrument (not shown) can be used to insert the sleeve 10 into attachment device 40 by applying pressure on one side of sleeve 10 and on the opposite side of attachment device 40 to bring the sleeve to the partially seated position of FIG. 2. This partially seated position attaches the sleeve 10 to device 40 about rod 1, and yet allows the sleeve 10/device 40 assembly to still slide along rod 1 to allow adjustment of their position along rod 1. Then a further suitable cincher-type instrument (not shown) is used to apply pressure to the one side of sleeve 10 and the opposite side of device 40 to bring these components together into the fully seated position of FIG. 3. This fully seated position locks or secures the attachment device 40 onto rod 1. Final locking of the attachment device 40 and the sleeve 10 to the rod 1, and thus final component fixation is obtained by the interference fit of the sleeve 10 between both the attachment device 10 and rod 1 at this fully seated position. It is noted that when the sleeve 10 is fully seated in the attachment device 40, the length of the sleeve (LS) is preferably fully contained within the length of the attachment device (LA).

The elongated spinal rod 1 may be any suitable length or any suitable diameter (D). The cylindrical rod 1 has a smooth outer surface. The sleeve 10 has a longitudinal cylindrical bore 16 therethrough for fitting about rod 1. The surface of the bore 16 is also smooth.

The sleeve 10 includes a first portion 15 and a second portion 25. The second portion is relatively shorter than the first portion. The first portion 15 includes a first outer taper 11 with a wide end 13 tapering to a narrow end 12. The second portion 25 includes a second outer reverse taper 21 with a narrow end 22 tapering to a wide end 23. The narrow end 12 of first taper 11 converges with the narrow end 22 of second taper 21 forming a reduced or narrowed portion. A recessed transition zone or groove 29 may be provided between the first and second tapers 11 and 21. The recessed transition zone 29 of sleeve 10 aligns with the edge 44 of counterbore 45 of device 40 when the sleeve 10 is fully seated therein. Thus, neither taper 11 or 21 of sleeve 10 is providing a line contact. The reverse taper 21 helps provide a locking position when the sleeve 10 is pushed to its fully seated position with the second portion 25 of sleeve 10 located in counterbore 45 of attachment device 40. This dual taper design provides an audible and force-feel feedback to the surgeon to communicate a positive lock of the sleeve 10 in the fully seated position in device 40. The reverse taper 21 of the sleeve 10 also allows the sleeve to be unlocked from the attachment device 40 with a suitable instrument (not shown) should removal of the sleeve 10 be necessary. The reverse taper 21 allows sleeve 10 to slide over the edge 44 of counterbore 45 in attachment device 40 facilitating such removal (as opposed to a sharp edge such as a 90 degree flange which would catch on edge 44 to resist removal). The counterbore 45 provides a retaining wall 55 to help lock dual taper sleeve 10 into its fully seated position.

The attachment device 40 includes an inner taper 51 having a wide end 53 tapering to a narrow end 54. A chamfer 52 extends from the wide end 53 of inner taper 51. The counterbore 45 is positioned at the narrow end 54 of taper 51 forming retaining wall 55 therebetween. When the sleeve 10 is positioned and fully seated between rod 1 and device 40, the first outer taper 11 mates with the inner taper 51 of device 40. The second portion 25 of sleeve 10 mates with counterbore 45 to secure device 40 to rod 1.

The sleeve 10 has an open back 17 extending the length (LS) of the sleeve 10. The open back 17 interconnects with bore 16. The attachment device 40 has an open back 57 extending the length (LA) of the attachment device 40. The open back of device 40 interconnects with inner taper 51 and counterbore 45. The open back 57 of device 40 allows rod 1 to easily drop into position. The open back 17 of the sleeve 10 has a width (WS), while the open back of the attachment device has a width (WA). The counterbore 45 includes a semicircular bottom wall 46 which extends into oppositely located straight side walls 47. The counterbore 45 between side walls 47 has a width (WC). The width (WC) of counterbore 45 is larger than the width (WA) of attachment device 40.

The second portion 25 of sleeve 10 includes a tapered rounded bottom surface 24 forming the second outer reverse taper 21 and two relief cuts 28 on opposite sides of second portion 25 forming two legs 26 extending from bottom surface 24. The depth of the relief cuts 28 can vary. These relief cuts 28 help give clearance to allow sleeve 10 to enter the taper 51 of attachment device 40. A retainment tab 27 extends from each leg 26. The retainment tabs 27 allow the sleeve 10 to maintain proper alignment within the attachment device. These retainment tabs help prevent rotation of sleeve 10 within attachment device 40, thus acting as antirotation tabs. The tabs 27 help engage the sleeve in the attachment device 40 in both the partially seated and fully seated positions. The retainment tabs 27 extend above the two longitudinal spaced upper edges 31 on either side of open back 17 of sleeve 10. A chamfer 18 extends from each upper edge 31 of sleeve 10 to a longitudinal lower edge 32. It is the distance between spaced lower edges 32 which creates the width (WS) of the open back 17 of sleeve 10. The distance between the upper edges 31 would be wider than width (WS) as the chamfer 18 extends outwardly from lower edges 32 to upper edges 31. The included angle between the two angled chamfered surfaces is about 60 degrees. The width (WS) of sleeve 10 is sufficient to enable the sleeve 10 to snap fit laterally onto rod 1 and laterally retain sleeve 10 on rod 1. The rod 1 has a diameter (D). The width (WS) of the open back 17 of sleeve 10 is slightly smaller than the diameter (D) of rod 1, but is large enough to snap fit laterally onto rod 1. The sleeve 10 can be snapped back off the rod, if needed. The ability to snap fit the sleeve 10 onto rod 1 allows the sleeve 10 to be easily positioned at the desired location on rod 1. While the sleeve 10 can still be slid onto the rod 1 from an end of the rod, the ability to snap the sleeve onto the rod laterally at any desired location along the rod 1 provides more versatility than designs in which the sleeve 10 has to be slid from an end of the rod 1.

The retainment tabs 27 each include an abutting tab face 37 to abut against retaining wall 55 of counterbore 45. This abutting relationship helps secure the sleeve 10 in the counterbore 45 of attachment device 40, and thus secure the sleeve 10 and attachment device to rod 1 in its fully seated position. When the sleeve 10 is fully seated in the attachment device 40, the bore 16 of sleeve 10 is frictionally retained on cylindrical rod 1, while the taper 51 of attachment device 40 is frictionally secured on first sleeve taper 11 with the second portion 25 of sleeve 10 secured and retained via the second reverse taper 21 and retainment tabs 27 in counterbore 45. The open back 17 of sleeve 10 enables the sleeve 10 to be compressed between the rod 1 and device 40 to create a secure friction fit therebetween. Thus, retention of the attachment device 40 and sleeve 10 to the rod 1 is accomplished by the locking of tapers 11 and 51 and the mechanical resistance of the second portion 25 or locking hub in the counterbore 45.

The upper longitudinal spaced edges 61 of device 40 created by the open back 57 include two oppositely located recessed cuts 58. These recessed cuts provide a locating position for accepting retainment tabs 27 therein to provide the partially seated position of FIG. 2. Thus, the open back 57 of device 40 enables sleeve 10 to be maintained in a partially seated position via the interconnection of recessed cuts 58 and tabs 27. The retainment tabs 27 each include a tapered leading edge 35. This tapered leading edge 35 helps allow the retainment tab to slide out of recessed cuts 58 in order to move the sleeve from the partially seated position to the fully seated position.

The sleeve 10 further includes a through slot 19 which is a relatively thinner opening than the open back 17 of sleeve 10. The through slot 19 extends longitudinally into sleeve 10 from the wide end 13 of the first portion 15 of sleeve 10. The through slot 19 terminates part way into the sleeve 10 in order to maintain the structural integrity of sleeve 10. The through slot 19 connects continuously with a partial slot 20 which extends the remainder of the length of the sleeve. The partial slot extends only partially into the thickness of sleeve 10 leaving a thin connecting portion 6 to maintain the structural integrity of sleeve 10. The slots 19 and 20 help give additional flexibility to sleeve 10 to aid in snap fitting the sleeve 10 to rod 1. The through slot 19 and partial slot 20 also provide additional compressibility to the sleeve to allow the sleeve 10 to be tightly compressed and secured between the rod 1 and device 40. The slotted sleeve 10 thus provides a press-fit interface to secure an attachment device 40 to a rod 1 with the sleeve press-fit therebetween.

The rod, sleeve, and attachment device components of the spinal implant system of the present invention may be made of any suitable surgical grade material. One such suitable material is a high-grade stainless steel, such as 22-13-5 stainless steel.

It is noted that the first taper 11 on the sleeve 10 and the mating inner taper 51 on attachment device 40 may each suitably about a 6 degree included taper, providing the necessary force for locking therebetween. The second reverse taper 21 on sleeve 10 may be about a 10 degree taper. However, these suggested tapers are not intended to be limiting. The diameter of bore 16 of sleeve 10 is suitably and matingly sized to be compressed about a rod 1 having diameter (D). Accordingly, the dimensions and sizes of the various components in this inventive system may be any suitable dimensions and sizes which enable the components to have the desired strength as needed, and the desired function as described herein.

While this invention has been described in terms of a particularly advantageous embodiment, those skilled in the art can appreciate that modifications can be made without departing from the spirit and scope of this invention.

We claim:

1. A spinal implant system including a spinal rod, an attachment device, and an interpositional sleeve for positioning between the rod and the attachment device for securing the attachment device to the rod, wherein the sleeve has a length and includes a longitudinal bore therethrough and an open back extending the length of the sleeve and connecting with the bore, and wherein the open back of the sleeve has a width sufficient to enable the sleeve to snap fit laterally onto the rod and laterally retain the sleeve on the rod, and wherein the rod has a diameter and the width of the open back of the sleeve is slightly smaller than the diameter of the rod, but is large enough to snap fit laterally onto the rod by passing the rod laterally through the open back of the sleeve.

2. A spinal implant system including a spinal rod, an attachment device, and an interpositional sleeve for securing the attachment device to the rod, wherein the attachment device includes a first means for partially seating the sleeve between the rod and the attachment device and a second means for fully seating the sleeve between the rod and the attachment device, and wherein the attachment device includes an open back providing two upper longitudinal spaced device edges and, the attachment device has a first end and a second end, and wherein the first means for partially seating the sleeve is provided in between the first and second ends of the device, and the second means for fully seating the sleeve if provided adjacent one of either the first or second ends of the device, and wherein the second means is longitudinally spaced from the first means on the attachment device.

3. The system of claim 2 wherein the first means comprises two oppositely located recessed cuts along the spaced device edges and the second means comprises a counterbore.

4. The system of claim 3 wherein the sleeve includes a retainment tab means for locating in either the first or second means.

5. The system of claim 3 wherein the sleeve includes an open back providing two longitudinal spaced sleeve edges and wherein the sleeve further includes a retainment tab on each of the spaced sleeve edges for locating in either the first or second means.

6. A spinal implant system including a spinal rod, an attachment device, and an interpositional sleeve for securing the attachment device to the rod, wherein the attachment device includes an inner taper and a counterbore at one end of the inner taper, and wherein the sleeve includes a retainment tab means extending therefrom for mating with the counterbore for providing alignment and antirotation of the sleeve in the attachment device.

7. A method of utilizing a spinal implant system including the steps of:

a) providing a spinal rod, an attachment device, and an interpositional sleeve, wherein the sleeve has a length and includes a longitudinal bore therethrough and an open back extending the length of the sleeve and connecting with the bore, and wherein the open back of the sleeve has a width sufficient to enable the sleeve to snap fit laterally onto the rod and laterally retain the sleeve on the rod, and wherein the rod has a diameter and the width of the open back of the sleeve is slightly smaller than the diameter of the rod, but is large enough to snap fit laterally onto the rod, such that the method further includes;

b) snap fitting the sleeve laterally onto the rod by passing the rod laterally through the open back of the sleeve; and c) then positioning the sleeve between the rod and the attachment device for securing the attachment device to the rod.

* * * * *